United States Patent [19]

Swainbank

[11] 4,402,560
[45] Sep. 6, 1983

[54] CONDUCTIVE WRIST STRAP

[76] Inventor: Sheila O. Swainbank, 3523 Flair Dr., Dallas, Tex. 75229

[21] Appl. No.: 282,778

[22] Filed: Jul. 13, 1981

[51] Int. Cl.³ ............................................. H01R 4/66
[52] U.S. Cl. .................................. 339/11; 339/14 R; 339/147 R
[58] Field of Search ........... 339/143 R, 147 P, 147 R, 339/14 R, 176 MP, 17 F, 11; 128/690, 639, 641

[56] References Cited

U.S. PATENT DOCUMENTS

| | | | |
|---|---|---|---|
| 4,112,941 | 9/1978 | Larimore | 128/641 |
| 4,280,506 | 7/1981 | Zurcher | 128/690 |

FOREIGN PATENT DOCUMENTS

| | | | |
|---|---|---|---|
| 984257 | 2/1965 | United Kingdom | 339/147 P |
| 1007358 | 10/1965 | United Kingdom | 339/147 R |

OTHER PUBLICATIONS

"Product Specification", Charleswater Products Inc. CP401R Statfree Wrist Strap.
Advertisement, Westcorp, "Electrically Conductive Wrist Straps W-0740 & W-0741.

*Primary Examiner*—Eugene F. Desmond
*Attorney, Agent, or Firm*—William J. Scherback

[57] ABSTRACT

A system is described for grounding individuals involved in the assembly or repair of electronic components that are electrostatic sensitive. The system includes a wrist strap of conductive material having one element of an electrical connector connected thereon. A length of copper ground lead is connected at one end by way of a resistor to a metal connecting element designed to meet with the connector on the wrist strap. A woven shield preferably of nylon completely encloses the ground lead and terminates adjacent to the connection to the resistor. A housing of insulating material is provided having a central portion for receiving the resistor and the end portions of the nylon braid and the copper ground lead. The receiving portion of the housing is filled with an insulated material such as epoxy firmly to bond the resistor and portions of the ground lead and insulating braid to the structure of the housing. The housing is also provided with a flange-like structure extending beyond the receiving portion to enable disconnection of the electrical contact by readily pulling up or otherwise applying force to the flange which reduces fatigue in the copper ground lead during a significant number of connections and disconnnections. There is also provided an electrical connecting means at the opposite end of the copper ground lead for making conductive connection to a ground position at a work station.

4 Claims, 4 Drawing Figures

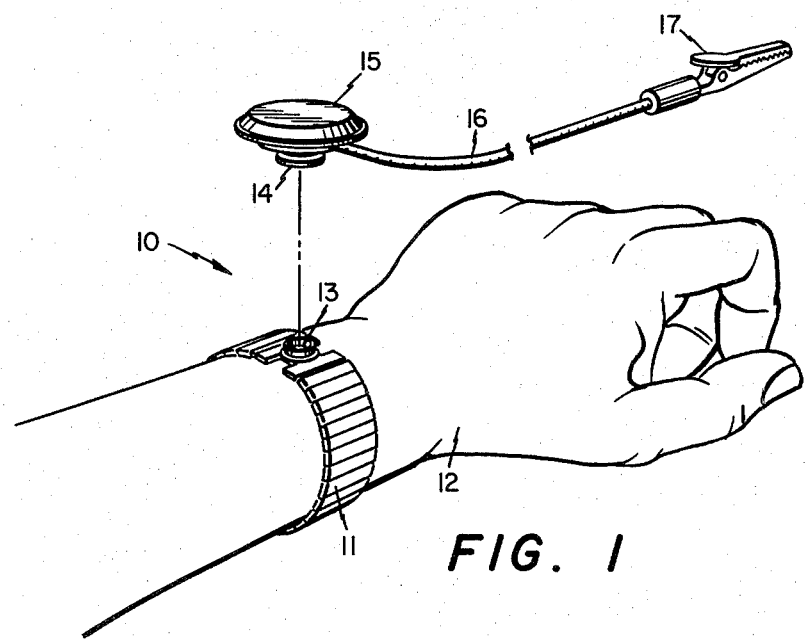
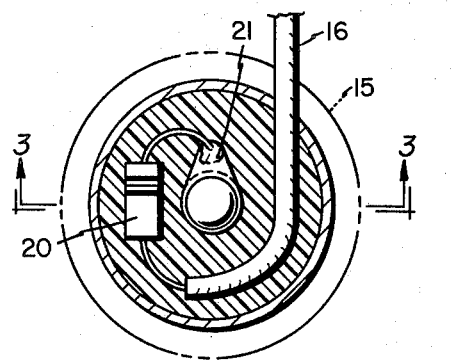
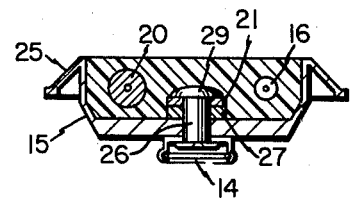
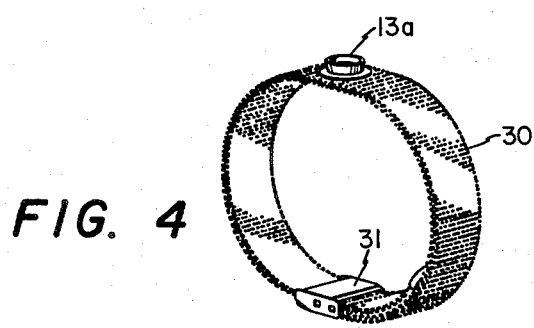
FIG. 1
FIG. 2
FIG. 3
FIG. 4

CONDUCTIVE WRIST STRAP

BACKGROUND OF THE INVENTION

1. Field of the Invention

The present invention relates in general to devices or systems for providing a conductive path to ground to dissipate static charges that have accumulated on personnel who are involved in the repair or assembly of microelectronic devices. More particularly the invention relates to a conductive wrist strap which is connected by way of a conductor to a suitable means for making electrical contact with a ground station. The suitable means may take the form of an alligator clip or a banana plug.

2. The Prior Art

It is common practice in the electronics industry to take steps to assure that individuals who are involved in the assembly or repair of microelectronic components, such as memory devices, are free of electrostatic charge so as to avoid effective destruction of the devices when the individual contacts them. If the individual has accumulated an electrostatic charge, the contact with the device would cause a discharge and effectively destroy the electronic component. To this end there have appeared a number of wrist straps for grounding personnel at work stations to enable them to work on sensitive components sensitive to static charge. In one instance the wrist strap is comprised of a conductive polyester wrist strap with a Velcro type fastener.

Another example of prior art wrist straps is one wherein an all textile strap is impregnated with a thermosetting conductive coating and fastened about the wrist of an operator. In all instances the wrist strap is connected by way of a swivel type snap connector and insulated conductor to a suitable device for making a connection to ground at the work station.

While all purport to provide for easy disconnection of the operator in order to leave the work station, they have in fact proven to be difficult so that operators to avoid breaking fingernails have resorted merely to pulling on the conductive wire which after a number of disconnections is weakened and in many cases broken, thus impairing the effectiveness of the ground connection. In other instances there have been provided high resistance elements in series with the conductor for the purpose of providing a safety measure by reducing the flow of current to an operator should the wire insulation become worn or frayed and thereafter the hand come in contact with a source of high voltage. In some instances the resistor has been provided in series in the conductor near the end to be connected to the ground station which does not afford any protection whatsoever under the circumstances outlined above. And in other instances the resistor has been placed near the wrist of the operator but by reason of continued connection and disconnection has resulted in a broken contact thereby rendering the wrist strap ineffective.

SUMMARY OF THE INVENTION

According to the present invention there is provided a system for grounding individuals involved in the assembly or repair of electronic components that are electrostatic sensitive. The assembly comprises a wrist strap of conductive material having one element of an electrical connector connected thereon. A length of copper ground lead is connected at one end by way of a resistor to a metal connecting element designed to meet with the connector on the wrist strap. A woven shield preferably of nylon completely encloses the ground lead and terminates adjacent to the connection to the resistor. A housing of insulating material is provided having a central portion for receiving the resistor and the end portions of the nylon braid and the copper ground lead. The receiving portion of the housing is filled with an insulated material such as epoxy firmly to bond the resistor and portions of the ground lead and insulating braid to the structure of the housing. The housing is also provided with a flange-like structure extending beyond the receiving portion to enable disconnection of the electrical contact by readily pulling up or otherwise applying force to the flange which reduces fatigue in the copper ground lead during a significant number of connections and disconnections. There is also provided an electrical connecting means at the opposite end of the copper ground lead for making conductive connection to a ground portion at a work station thereby establishing an electrical path to dissipate any static charges that might otherwise accumulate on the person performing the assembly or repair operations.

A BRIEF DESCRIPTION OF THE DRAWINGS

In the accompanying drawings:

FIG. 1 illustrates the system of the present invention;

FIG. 2 is an enlargement of a "button" housing, a protective resistor and the end of a conductor;

FIG. 3 is a cross section of the housing taken along line 3—3 of FIG. 2; and

FIG. 4 illustrates another and preferred form of wrist bracelet to be utilized in the system of the present invention.

DETAILED DESCRIPTION

Referring now to FIG. 1 the reference character 10 generally indicates the system of the present invention which in the embodiment illustrated comprises an expandable wristband 11 of the type commonly found in conjunction with wristwatches mounted about the wrist 13 of an operator. Mounted to a plate secured at opposite ends of the flexible wristband 11 is the male end of a snap connector 13 adapted to receive the female end 14 mounted to a housing assembly 15. The connector of the type illustrated affords flexibility in that the mating portions 13 and 14 are free to rotate one with respect to the other while at the same time affording continuous electrical connection. Extending from the housing 15 is a conductor 16 which, as will be shown, electrically connects the female member 14 of the connecting assembly to a suitable connecting means such as the alligator clip 17 which will be used to make electrical contact to a ground point at a work station.

The housing 15 is made of insulating material such as polyethylene of some other suitable plastic material and in its center core is recessed to provide a receiving means for a resistor 20 and one end of the conductor assembly 16. The conductor assembly 16 is comprised of a conductive wire of approximately 18 gauge surrounded by a woven shield of insulating material which preferably is formed of nylon or Fiberglas. One end of the resistor 20, which is of a high impedance such for example as one megohm, is connected to terminal 21 in electrical contact with the female end 14 of the contact assembly and at whose opposite end is connected to the conductor assembly 16.

As better shown in FIG. 3, the female end 14 of the contact assembly is mounted to the housing by way of a rivet 26 having a head portion 29. Between the head of the rivet and the body assembly is placed a washer 27 and the electrical terminal 21. After assembly of the components in the housing 15 the recess is filled with a compound such as an epoxy to establish a rigid relationship between the components such as the resistor 20, the conductor 16 and the housing and also to provide for effectively hermetically sealing these elements within the housing.

The housing which is circular in configuration is provided with overhang or a flange portion 25 which enables an operator readily to disconnect the male and female connectors by slipping at least two digits of hand under the flanges and exerting an upward pressure. This avoids the practice of making a disconnection by pulling up on the conductor assembly 16.

While the expandable bracelet 11 of FIG. 1 is very convenient inasmuch as it may readily be slipped over wrists of varying size and still maintain excellent electrical contact it would be preferred to provide a wristband which while flexible would resist expansion whenever the operator attempted to disconnect himself from the housing 15. Such a preferred form of wristband is illustrated in FIG. 4. There the wristband 30 is comprised of woven material made up of any suitable conductive type which in its open position can be wrapped around the wrist and then secured by way of the locking mechanism 31. Like the wristband 11 of FIG. 1 the wristband 30 of FIG. 4 is provided with the male 13a element of the connecting assembly.

It is obvious from the above description that the system of the present invention provides the optimum in establishing a static discharge path from an operator to a ground point at a work station, in that critical elements such as the resistor 20 and the connecting end of the conductor assembly 16 are firmly imbedded within the recess of the housing 15 which in turn is provided with features for establishing ready removal from or connection to the wrist of the operator.

Now that the principles of the invention have been described, modifications may be obvious to those skilled in the art and are intended to be within the scope of the following claims.

What is claimed is:

1. A system for electrically grounding individuals involved in the assembly of electronic components that are electrostatic sensitive comprising:
   a wrist strap of conductive material having an electrical connector mounted thereon;
   a housing of insulating material having a circular, horizontal cross-section and a central recessed portion;
   a mating electrical connector secured to an exterior of an underside of said housing and having a terminal extending into said recessed portion;
   a resistor within said recessed portion having one end electrically connected to said terminal;
   a length of conducting ground lead extending into said recessed portion and electrically connected to an opposite end of said resistor;
   a shield of insulation encompassing said ground lead and extending into said recessed portion to a position adjacent the lead connection to said resistor;
   said recessed portion being filled with an insulating material firmly to bound said resistor and end portions of said ground lead and said shield of insulation to said housing;
   said housing having a flange extending circumferentially of said housing opposite said electrical connectors and being sufficiently large to enable the disconnection of the contact between said connectors by the insertion of at least two digits of a hand under diametrically opposed portions of said flange in order to reduce the introduction of fatigue which otherwise might break said conducting ground lead after a number of connections and disconnections between said connectors;
   and electrical connecting means at the opposite end of said connecting ground lead for making a conductive connection to a ground at a work station in order to dissipate any electrostatic charges that might otherwise accumulate on the person of the individual and therefore avoid rendering defective the electronic components being assembled.

2. The system of claim 1 wherein said wrist strap is an expandable metal bracelet.

3. The system of claim 1 wherein said wrist strap is a flexible metal bracelet to be fixed in non-expandable relation to a wrist.

4. The system of claim 1 wherein said insulating material is an epoxy resin.

* * * * *